(12) United States Patent
McCabe (10) Patent No.: US 7,708,849 B2
(45) Date of Patent: May 4, 2010

(54) APPARATUS AND METHOD FOR CUTTING ELASTIC STRANDS BETWEEN LAYERS OF CARRIER WEBS

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 1048 days.

(21) Appl. No.: 11/324,923

(22) Filed: Jan. 4, 2006

(65) Prior Publication Data

US 2006/0130964 A1     Jun. 22, 2006

Related U.S. Application Data

(63) Continuation-in-part of application No. 10/828,095, filed on Apr. 20, 2004, now abandoned.

(51) Int. Cl.
*B32B 37/00* (2006.01)

(52) U.S. Cl. .................. 156/73.1; 156/204; 156/267; 156/269

(58) Field of Classification Search ............... 156/73.1, 156/73.3, 196, 204, 229, 267, 269, 160, 161, 156/163, 164
See application file for complete search history.

(56) References Cited

U.S. PATENT DOCUMENTS

| | | | |
|---|---|---|---|
| 135,145 A | 1/1873 | Murphy | |
| 293,253 A | 2/1884 | Purvis | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |

(Continued)

FOREIGN PATENT DOCUMENTS

BE     1007854     11/1995

(Continued)

OTHER PUBLICATIONS

Reciprocating Mechanisms, Ingenious Mechanisms for Designers and Inventors, Franklin Jones vol. 1.

(Continued)

*Primary Examiner*—James Sells
(74) *Attorney, Agent, or Firm*—Ryan Kromholz & Manion, S.C.

(57) ABSTRACT

A method of utilizing a scrim of elastic material including cutting the elastic strands within a disposable undergarment is disclosed. The method generally follows the steps of providing two webs of fabric and an elastic scrim of mesh-like design, adhering the scrim between the two webs of fabric, determining areas where elastic material is not required, compressing the non-elastic areas with a thermal compression tool, and forming a disposable undergarment.

12 Claims, 6 Drawing Sheets

U.S. PATENT DOCUMENTS

| | | |
|---|---|---|
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller Jr. |
| 3,470,848 A | 10/1969 | Dreher |
| 3,484,275 A | 12/1969 | Lewicki Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |

| Patent | Type | Date | Inventor |
|---|---|---|---|
| 4,642,150 | A | 2/1987 | Stemmler |
| 4,642,839 | A | 2/1987 | Urban |
| 4,650,530 | A | 3/1987 | Mahoney et al. |
| 4,663,220 | A | 5/1987 | Wisneski et al. |
| 4,672,705 | A | 6/1987 | Bors et al. |
| 4,675,062 | A | 6/1987 | Instance |
| 4,693,056 | A | 9/1987 | Raszewski |
| 4,701,239 | A | 10/1987 | Craig |
| 4,726,874 | A | 2/1988 | VanVliet |
| 4,726,876 | A | 2/1988 | Tomsovic et al. |
| 4,743,241 | A | 5/1988 | Igaue et al. |
| 4,751,997 | A | 6/1988 | Hirsch |
| 4,753,429 | A | 6/1988 | Irvine et al. |
| 4,756,141 | A | 7/1988 | Hirsch et al. |
| 4,764,325 | A | 8/1988 | Angstadt |
| 4,765,780 | A | 8/1988 | Angstadt |
| 4,776,920 | A | 10/1988 | Ryan |
| 4,777,513 | A | 10/1988 | Nelson |
| 4,782,647 | A | 11/1988 | Williams et al. |
| 4,785,986 | A | 11/1988 | Daane et al. |
| 4,795,510 | A | 1/1989 | Wittrock et al. |
| 4,801,345 | A | 1/1989 | Dussaud et al. |
| 4,802,570 | A | 2/1989 | Hirsch et al. |
| 4,840,609 | A | 6/1989 | Jones et al. |
| 4,845,964 | A | 7/1989 | Bors et al. |
| 4,864,802 | A | 9/1989 | D'Angelo |
| 4,880,102 | A | 11/1989 | Indrebo |
| 4,888,231 | A | 12/1989 | Angstadt |
| 4,892,536 | A | 1/1990 | Des Marais et al. |
| 4,904,440 | A | 2/1990 | Angstadt |
| 4,908,175 | A | 3/1990 | Angstadt |
| 4,909,019 | A | 3/1990 | Delacretaz et al. |
| 4,925,520 | A | 5/1990 | Beaudoin et al. |
| 4,927,322 | A | 5/1990 | Schweizer et al. |
| 4,927,582 | A | 5/1990 | Bryson |
| 4,937,887 | A | 7/1990 | Schreiner |
| 4,963,072 | A | 10/1990 | Miley et al. |
| 4,987,940 | A | 1/1991 | Straub et al. |
| 4,994,010 | A | 2/1991 | Doderer-Winkler |
| 5,000,806 | A | 3/1991 | Merkatoris et al. |
| 5,021,111 | A | 6/1991 | Swenson |
| 5,025,910 | A | 6/1991 | Lasure et al. |
| 5,045,039 | A | 9/1991 | Bay |
| 5,062,597 | A | 11/1991 | Martin et al. |
| 5,064,179 | A | 11/1991 | Martin |
| 5,080,741 | A | 1/1992 | Nomura et al. |
| 5,094,658 | A | 3/1992 | Smithe et al. |
| 5,096,532 | A | 3/1992 | Neuwirth et al. |
| 5,108,017 | A | 4/1992 | Adamski et al. |
| 5,109,767 | A | 5/1992 | Nyfeler et al. |
| 5,110,403 | A | 5/1992 | Ehlert |
| 5,127,981 | A | 7/1992 | Straub et al. |
| 5,131,525 | A | 7/1992 | Musschoot |
| 5,147,487 | A | 9/1992 | Nomura et al. |
| 5,163,594 | A | 11/1992 | Meyer |
| 5,171,239 | A | 12/1992 | Igaue et al. |
| 5,176,244 | A | 1/1993 | Radzins et al. |
| 5,183,252 | A | 2/1993 | Wolber et al. |
| 5,188,627 | A | 2/1993 | Igaue et al. |
| 5,195,684 | A | 3/1993 | Radzins |
| 5,203,043 | A | 4/1993 | Riedel |
| 5,213,645 | A | 5/1993 | Nomura et al. |
| 5,223,069 | A | 6/1993 | Tokuno et al. |
| 5,226,992 | A | 7/1993 | Morman |
| 5,246,433 | A | 9/1993 | Hasse et al. |
| 5,267,933 | A | 12/1993 | Precoma |
| 5,308,345 | A | 5/1994 | Herrin |
| 5,328,438 | A | 7/1994 | Crowley |
| 5,340,424 | A | 8/1994 | Matsushita |
| 5,368,893 | A | 11/1994 | Sommer et al. |
| 5,407,513 | A | 4/1995 | Hayden et al. |
| 5,415,649 | A | 5/1995 | Watanabe et al. |
| 5,421,924 | A | 6/1995 | Ziegelhoffer et al. |
| 5,424,025 | A | 6/1995 | Hanschen et al. |
| 5,429,576 | A | 7/1995 | Doderer-Winkler |
| 5,435,802 | A | 7/1995 | Kober |
| 5,449,353 | A | 9/1995 | Watanabe et al. |
| 5,464,401 | A | 11/1995 | Hasse et al. |
| 5,486,253 | A | 1/1996 | Otruba |
| 5,494,622 | A | 2/1996 | Heath et al. |
| 5,531,850 | A | 7/1996 | Herrmann |
| 5,540,647 | A | 7/1996 | Weiermann et al. |
| 5,545,275 | A | 8/1996 | Herrin et al. |
| 5,545,285 | A | 8/1996 | Johnson |
| 5,552,013 | A | 9/1996 | Ehlert et al. |
| 5,556,360 | A | 9/1996 | Kober et al. |
| 5,556,504 | A | 9/1996 | Rajala et al. |
| 5,560,793 | A | 10/1996 | Ruscher et al. |
| 5,602,747 | A | 2/1997 | Rajala |
| 5,624,420 | A | 4/1997 | Bridges et al. |
| 5,624,428 | A | 4/1997 | Sauer |
| 5,628,738 | A | 5/1997 | Suekane |
| 5,634,917 | A | 6/1997 | Fujioka et al. |
| 5,643,165 | A | 7/1997 | Klekamp |
| 5,643,396 | A | 7/1997 | Rajala et al. |
| 5,645,543 | A | 7/1997 | Nomura et al. |
| 5,659,229 | A | 8/1997 | Rajala |
| 5,660,657 | A | 8/1997 | Rajala et al. |
| 5,660,665 | A | 8/1997 | Jalonen |
| 5,683,376 | A | 11/1997 | Kato et al. |
| RE35,687 | E | 12/1997 | Igaue et al. |
| 5,693,165 | A | 12/1997 | Schmitz |
| 5,699,653 | A | 12/1997 | Hartman et al. |
| 5,707,470 | A | 1/1998 | Rajala et al. |
| 5,711,832 | A | 1/1998 | Glaug et al. |
| 5,725,518 | A | 3/1998 | Coates |
| 5,745,922 | A | 5/1998 | Rajala et al. |
| 5,746,869 | A | 5/1998 | Hayden et al. |
| 5,749,989 | A | 5/1998 | Linman et al. |
| 5,788,797 | A | 8/1998 | Herrin et al. |
| 5,817,199 | A | 10/1998 | Brennecke et al. |
| 5,829,164 | A | 11/1998 | Kotitschke |
| 5,836,931 | A | 11/1998 | Toyoda et al. |
| 5,858,012 | A | 1/1999 | Yamaki et al. |
| 5,865,393 | A | 2/1999 | Kreft et al. |
| 5,868,727 | A | 2/1999 | Barr et al. |
| 5,876,027 | A | 3/1999 | Fukui et al. |
| 5,876,792 | A | 3/1999 | Caldwell |
| 5,879,500 | A | 3/1999 | Herrin et al. |
| 5,902,431 | A | 5/1999 | Wilkinson et al. |
| 5,932,039 | A | 8/1999 | Popp et al. |
| 5,938,193 | A | 8/1999 | Bluemle et al. |
| 5,964,970 | A | 10/1999 | Woolwine et al. |
| 6,036,805 | A | 3/2000 | McNichols |
| 6,043,836 | A | 3/2000 | Kerr et al. |
| 6,050,517 | A | 4/2000 | Dobrescu et al. |
| 6,074,110 | A | 6/2000 | Verlinden et al. |
| 6,076,442 | A | 6/2000 | Arterburn et al. |
| 6,098,249 | A | 8/2000 | Toney et al. |
| 6,123,792 | A | 9/2000 | Samida et al. |
| 6,171,432 | B1 | 1/2001 | Brisebois et al. |
| 6,183,576 | B1 | 2/2001 | Couillard et al. |
| 6,210,386 | B1 | 4/2001 | Inoue |
| 6,212,859 | B1 | 4/2001 | Bielik, Jr. et al. |
| 6,250,048 | B1 | 6/2001 | Linkiewicz |
| 6,264,784 | B1 | 7/2001 | Menard et al. |
| 6,276,421 | B1 | 8/2001 | Valenti et al. |
| 6,306,122 | B1 | 10/2001 | Narawa et al. |
| 6,309,336 | B1 | 10/2001 | Muessig et al. |
| 6,312,420 | B1 | 11/2001 | Sasaki et al. |
| 6,314,333 | B1 | 11/2001 | Rajala et al. |
| 6,315,022 | B1 | 11/2001 | Herrin et al. |
| 6,336,921 | B1 | 1/2002 | Kato et al. |
| 6,358,350 | B1 | 3/2002 | Glaug et al. |
| 6,369,291 | B1 | 4/2002 | Uchimoto et al. |
| 6,375,769 | B1 | 4/2002 | Quereshi et al. |

| | | | | | |
|---|---|---|---|---|---|
| 6,391,013 B1 | 5/2002 | Suzuki et al. | 2007/0074953 A1 | 4/2007 | McCabe |
| 6,416,697 B1 | 7/2002 | Venturino et al. | | | |
| 6,443,389 B1 | 9/2002 | Palone | | | |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 0206208 | 12/1986 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO9747265 | 12/1997 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

| | | |
|---|---|---|
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B1 | 8/2003 | Anderson et al. |
| 6,605,173 B2 * | 8/2003 | Glaug et al. ............ 156/204 |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,743,324 B2 | 6/2004 | Hargett et al. |
| 6,766,817 B2 | 7/2004 | da Silva |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,066,586 B2 | 6/2006 | da Silva |
| 7,077,393 B2 | 7/2006 | Ishida |
| 7,172,666 B2 | 2/2007 | Groves et al. |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2003/0000620 A1 | 1/2003 | Herrin et al. |
| 2003/0015209 A1 | 1/2003 | Gingras et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0112517 A1 | 6/2004 | Groves et al. |
| 2004/0164482 A1 | 8/2004 | Edinger |
| 2005/0000628 A1 | 1/2005 | Norrby |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |

OTHER PUBLICATIONS

U.S. Appl. No. 10/828,095; Office Communication, Restriction Requirement; Oct. 5, 2005; 5pgs.

U.S. Appl. No. 10/828,095; Confirmation of Election; Amendment A; Oct. 19, 2005; 1pg.

U.S. Appl. No. 10/828,095; Office Communication, Restriction Requirement; Dec. 30, 2005.

U.S. Appl. No. 10/828,095; Response to Restriction Requirement; Amendment B; Feb. 27, 2006; 3pgs.

U.S. Appl. No. 10/828,095; Office Communication, May 18, 2006; 5pgs.

U.S. Appl. No. 10/828,095; Response to Office Action; Amendment C; Nov. 20, 2006; 5pgs.

U.S. Appl. No. 10/828,095; Petition for Withdrawal From Issue-Issue Fee Paid, Apr. 9, 2007; 1pg.

U.S. Appl. No. 10/828,095; Request for Continued Examination, Apr. 9, 2007; 1pg.

U.S. Appl. No. 10/828,095; Office Communication, Aug. 8, 2007; 5pgs.

U.S. Appl. No. 10/828,095; Response to Office Action; Amendment D; Nov. 8, 2007; 5pgs.

U.S. Appl. No. 10/828,095; Final Office Communication, Jan. 25, 2008; 5pgs.

U.S. Appl. No. 10/828,095; Office Communication-Notice of Abandonment, Aug. 20, 2008; 2pgs.

* cited by examiner

APPARATUS AND METHOD FOR CUTTING ELASTIC STRANDS BETWEEN LAYERS OF CARRIER WEBS

RELATED APPLICATION

This application is a continuation-in-part of application U.S. Ser. No. 10/828,095, filed 20 Apr. 2004, now abandoned.

BACKGROUND OF THE INVENTION

Disposable diapers of the children's training pant type, or of the adult incontinence type, are typically equipped with elastic strands, which generally encircle the waistband area and leg-holes. These strands of elastic are typically captured with adhesive between two layers of nonwoven materials. Various methods are used to position these elastic strands so that they produce the desired effect in the desired areas.

Several methods of cutting elastic strands in diaper manufacturing exist. One method of cutting the strands is to sever them ultrasonically, as described in U.S. Pat. No. 5,660,657. As taught in U.S. Pat. No. 5,707,470, an ultrasonic device can be used to sever elastic members, while the carrier webs that encapsulate the elastics are left intact.

One problem associated with prior art severing lies in the tendency of the unsecured severed ends of elastic to retract to some point beyond the limits of any adhesive pattern that is used to anchor the elastic strands to their carriers. Thus, the elastic strands are not controlled or anchored near the ends of the adhesion pattern and may snap back further into the adhesive pattern than desired. This results in an incomplete elastic pattern and poor product characteristics.

The problem remains of efficiently and securely placing elastic in the undergarment in such a manner that the elastic is still effective after severing the elastic. Securing elastic strands around the back and front waists, for example, in a secure and systematic manner is conducive to high speed manufacturing associated with diaper manufacturing.

SUMMARY OF THE INVENTION

The present invention concerns diapers and disposable undergarments having layers of elastic material and methods for producing such undergarments. The elastic material comprises a scrim or mesh-style pattern. The scrim retains its shape and flexibility, even after being applied within a diaper.

Generally, a web of fabric is laid down and an adhesive is placed upon the fabric. The scrim is then placed upon the fabric and a second web of fabric is placed on top of the scrim. The webs of fabric are then sealed to each other, thereby sealing the scrim between the layers of fabric.

Once the fabric layers are sealed together into a single web, the single web may be folded and bonded to form a diaper. Typically a diaper is bonded using a thermal or ultrasonic method. When this occurs, the inner elastic material will be melted and severed at the point of the bond. Normally this results in potential loss of elasticity as elastic strands may come loose or snap back when severed. However, the present invention allows the elastic material to retain its shape, even after severing.

The present invention also allows quicker and easier placement of the elastic material within the webs of material. Not every area within an undergarment is desired to be elastic. The present method allows the use of heat compression to remove specific areas of elastic material after being placed between the two webs of fabric. For instance, in certain applications, elastic material is generally not necessary or wanted below the waistline of a diaper wearer. The areas where the webs of fabric are to be bonded do not need elastic material present, either. By using heat that severs and melts the elastic while retaining the required elasticity, the present method allows for the possibility to form such non-elastic areas after the webs of fabric are sealed together.

Thus, the present invention generally follows the steps of providing two webs of fabric and an elastic scrim, adhering the scrim between the two webs of fabric, determining areas where elastic material is not required, compressing the non-elastic areas with a thermal compression tool, and forming a diaper garment. These steps will be more evident with the following detailed description and drawings.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention.

Figure 1A:
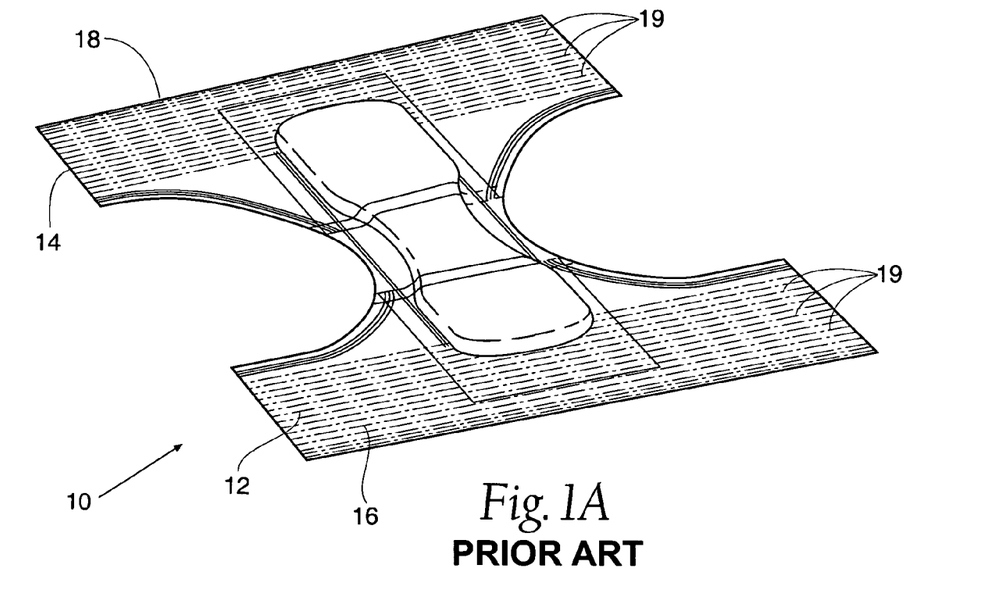
FIG. 1A shows a layout of an undergarment of the prior art having elastic strands.
Figure 1B:
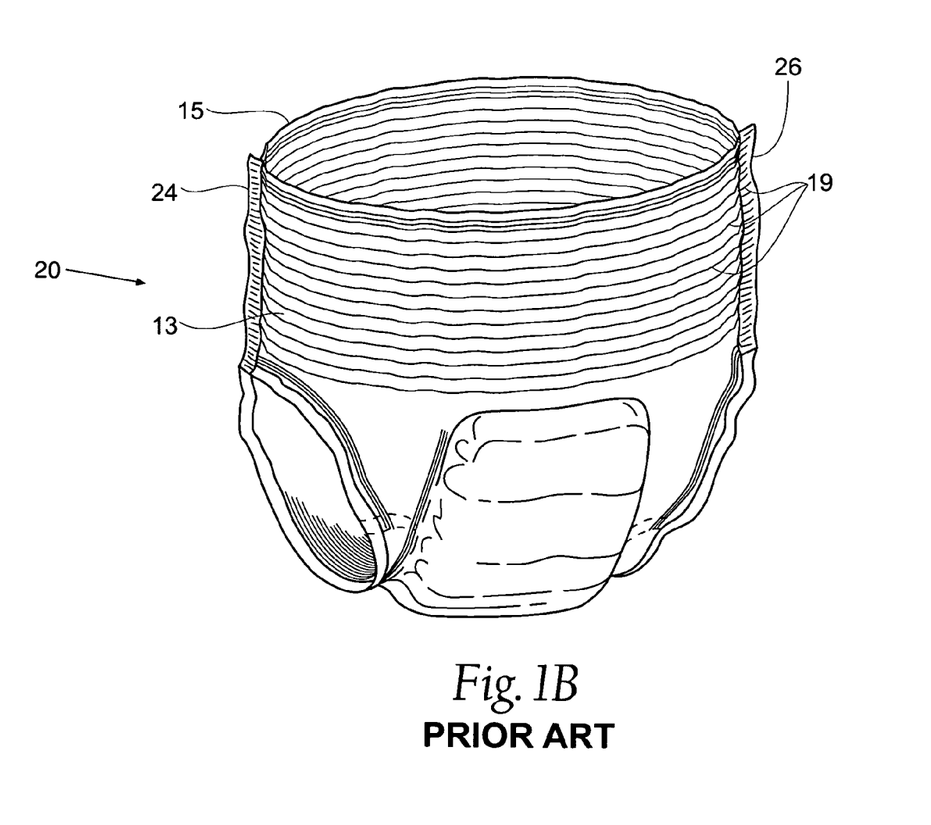
FIG. 1B shows an undergarment having elastic strands formed according to the prior art.

FIG. 1A shows a perspective view of a prior art undergarment blank 10. The blank 10 is of a symmetrical design having a first half 12 and a second half 14. As shown in FIG. 1B, the first half 12 will form a front portion 13 of an undergarment 20 and the second half 14 will form a back portion 15 of the undergarment 20. Elastic sections 16 and 18 are located within the first half 12 and the second half 14, respectively. The elastic sections 16 and 18 are made up of a plurality of individual elastic strands 19. Such a design allows for the specific designated areas of the undergarment 20 to have elastic properties instead of the entire undergarment.

However, when the first half 12 and the second half 14 are sealed together along edges 24 and 26, as known in the art, the elastic strands 19 may be severed, which can cause the elastic strands 19 not to be retained within the edges 24 and 26. Consequently, the strands 19 may become loose and snap out of place, affecting the elasticity of the undergarment 20, possibly even causing unwanted bunching in areas. The elastic/scrim is secured between the layers of non-woven with adhesive, except in side seal areas 24 and 26.

Figure 2:
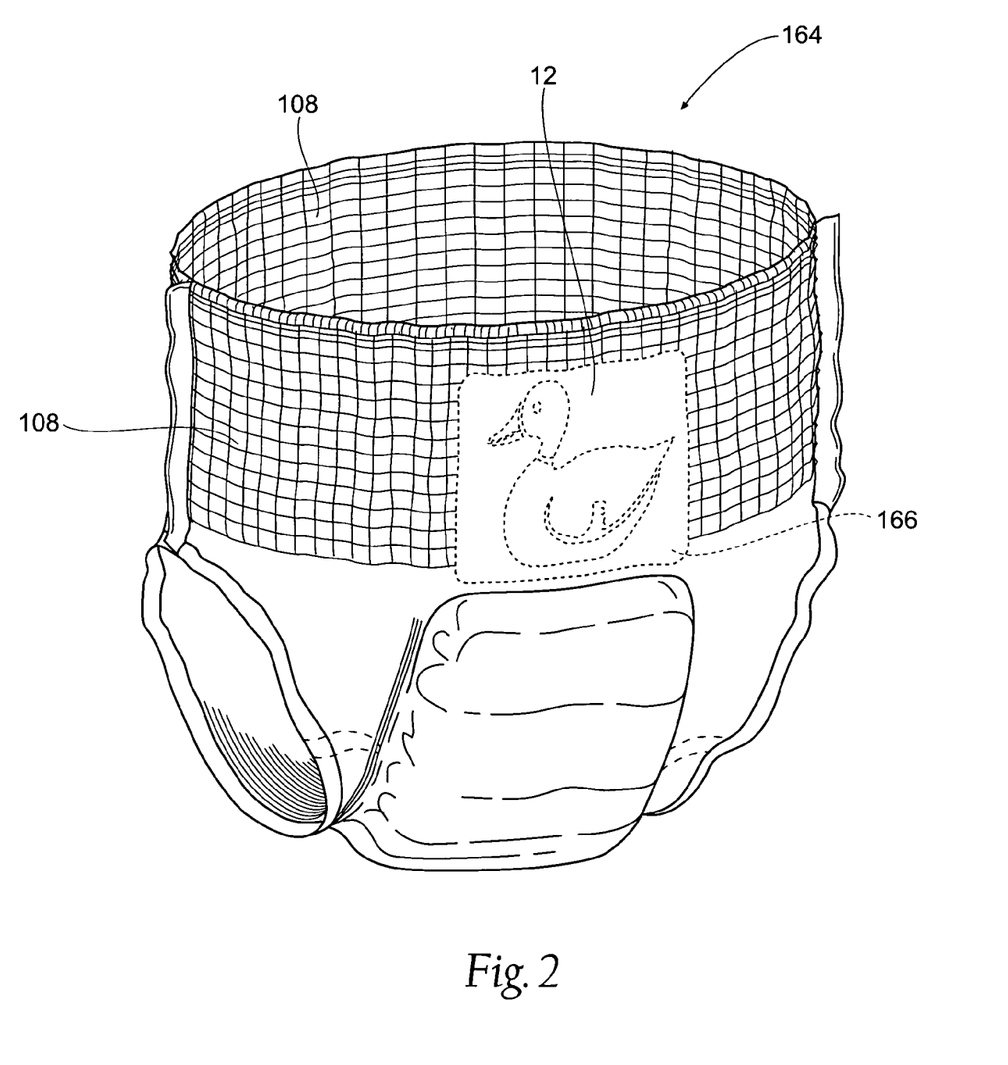
FIG. 2 is a perspective view of an embodiment of an undergarment formed according to the present invention.

FIG. 2 shows a diaper 164 made according to the present invention which has a patch 166 in the front of a diaper 164 where a zone of desired inelasticity 2 is provided for, whereby the elastic material is in a deactivated state in the zone 2. For instance, it is desirable in application of graphics as shown to have a zone of inelasticity for both comfort and for ease in printing/viewing the graphics.

Figure 3:
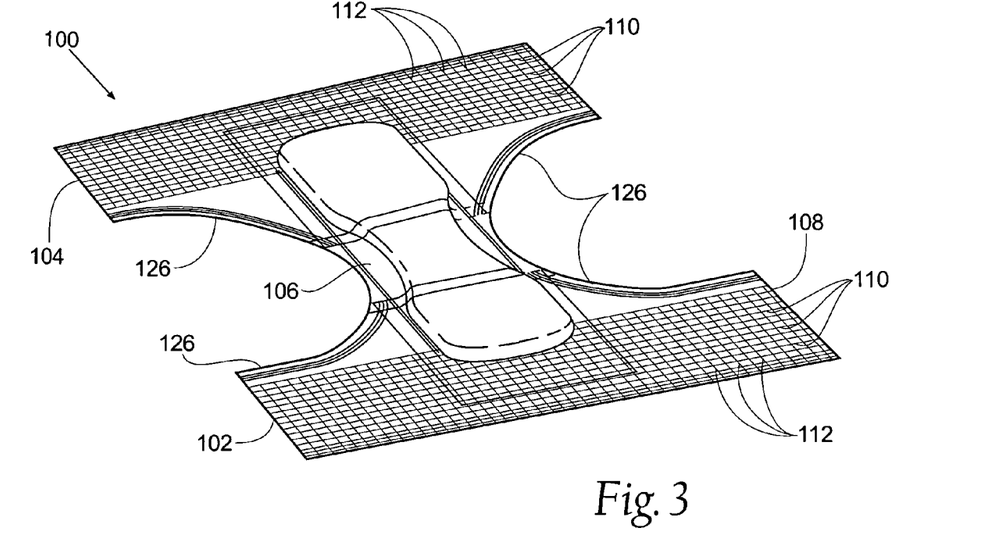
FIG. 3 shows an embodiment of a layout having elastic strands formed according to the present invention.

A perspective view of a web blank 100 formed according to the present invention is shown in FIG. 3. The blank 100 can be of symmetrical design, having a first half 102 and a second half 104. The blank 100 may contain an absorbent section 106, but is not necessary for the purpose of this invention. The first half 102 and the second half 104 further contain an elastic web or scrim 108. The scrim 108 has a mesh-like design, with both horizontal strands 110 and vertical strands 112. The horizontal strands 110 and the vertical strands 112 are formed from the same elastic material. The perpendicular overlap of the strands 110 and 112 creates a retaining force that allows the scrim 108 to retain its shape even if some of the strands have been severed. Thus, the scrim 108 is ideal for use in a disposable undergarment making method where heat compression tools are utilized to bond and seal the undergarment.

Figure 4:
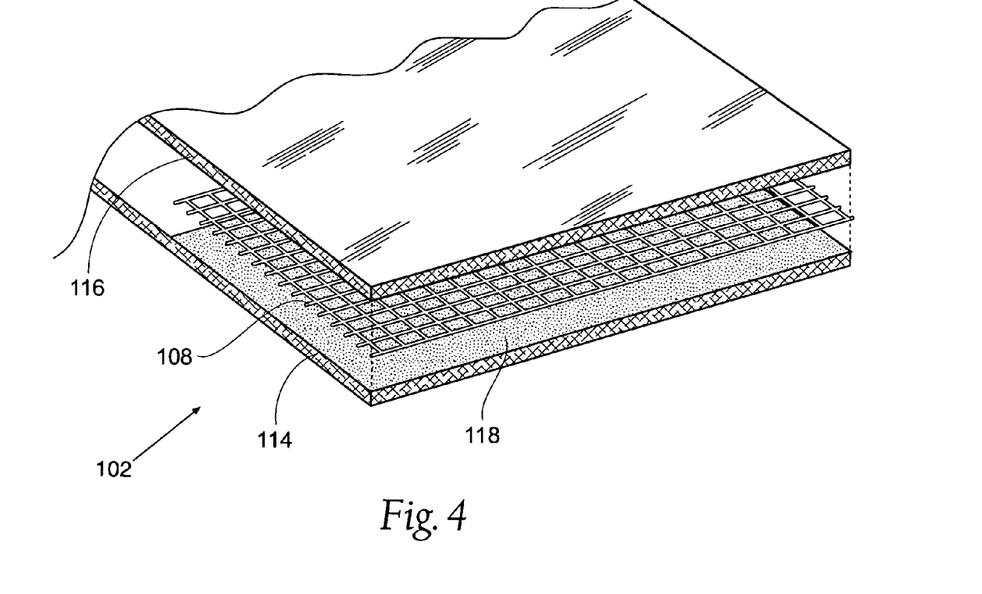
FIG. 4 is an exploded sectional view of the embodiment shown in FIG. 3.

FIG. 4 shows an exploded sectional perspective view of the first half 102. The use of the first half 102 is merely exemplary, and FIG. 4 could represent the second half 104, or another section of the blank 100 where the scrim 108 has been applied, as well. The scrim 108 is placed between a first layer of material 114 and a second layer of material 116. The layers of material 114 and 116 may be laminated, absorbent, or a combination of the two. For the purpose of this invention, it is not important specifically what composes the layers of material 114 and 116. Preferably, however, the layers 114 and 116 are made of nonwoven fabric webs. An adhesive 118 is placed upon the first layer 114. The scrim 108 is placed upon the first layer 114, with the scrim 108 having a predetermined tension. Any method or machine that will stretch the scrim 108 to the desired tautness will be sufficient to carry out the present invention. The second layer 116 is then compressed over the first layer 114 and the scrim 108, thereby securing the scrim 108 between the layers 114 and 116. The layering process normally takes process before the material is cut into the individual blanks 100 shown in FIG. 2. It should be noted that the adhesive 118 could also be applied to the second layer 116. Likewise, the adhesive 118 should be interpreted broadly as any means to secure the scrim 108 between the layers 114 and 116 and to secure the layers 114 and 116 to one another.

Figure 5:
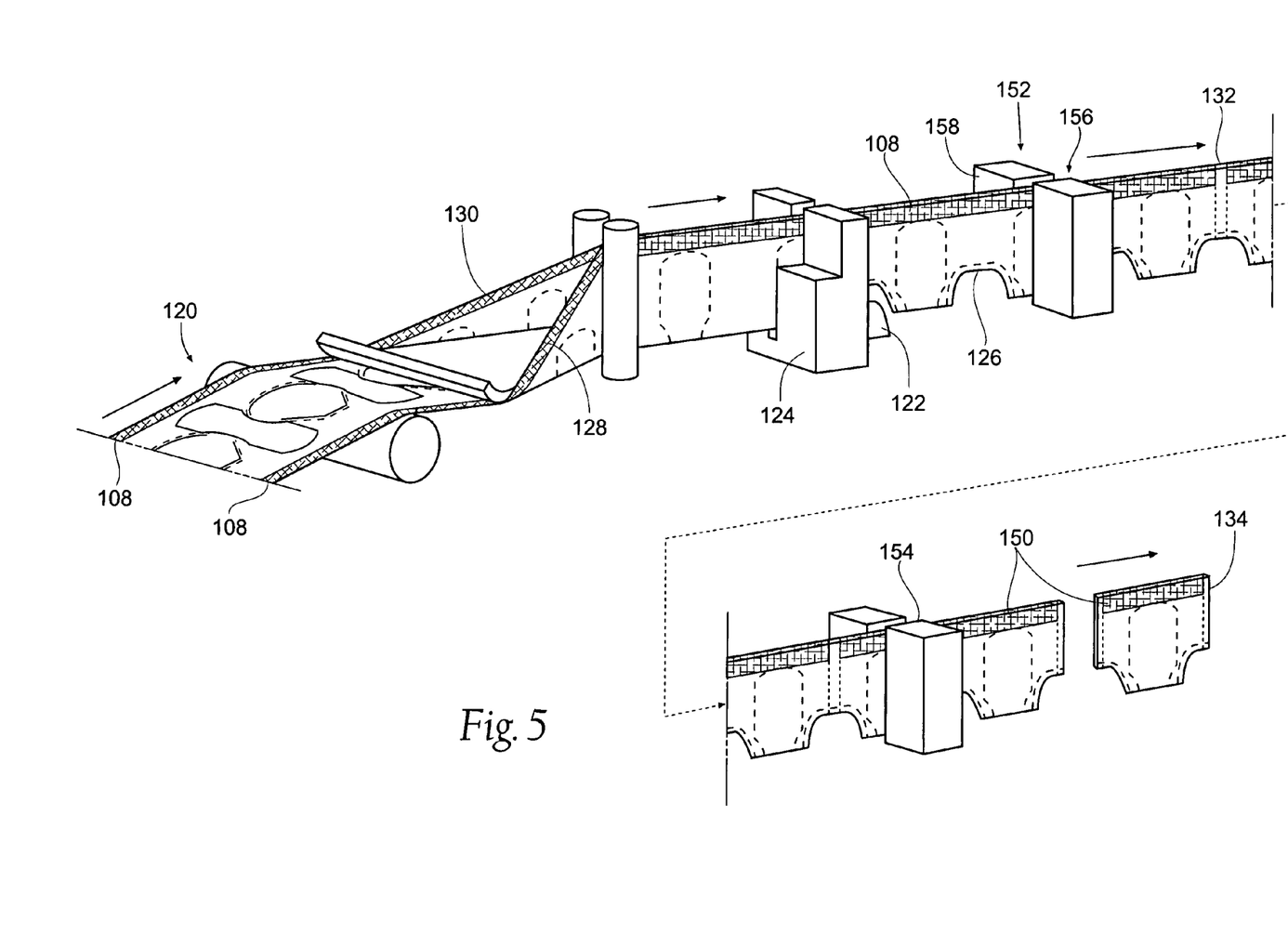
FIG. 5 is a schematic view of a process to form an undergarment according to the present invention.

Once the scrim 108 has been compressed and adhered between the layers 114 and 116, a continuous web of material 120 is fed through an assembly line, as the schematic representation in FIG. 5 shows. Leg hole materials 122, if not previously removed, are cut at a cutting station 124, thereby removing the material 122 contained within an approximate perimeter defined by the curved pattern of leg elastics 126 (see FIG. 1). The continuous web of material 120 is folded, before or after cutting out of the leg holes, longitudinally along its centerline, thereby aligning a front waist edge 128 with a back waist edge 130. A sealing device 152 then welds regions 132, which are to become side seams 134 of undergarments 150, either ultrasonically or by heat.

Note that the leg-holes are preferably cut out before this point, leaving only a narrow zone for welding. The weld pattern is preferably wide enough to extend into both the left side seam of one garment 150 and the right side seam of the adjacent garment 150. The garments 150 are then separated by passing through a cut-off knife assembly 154, which severs the web along the transverse axis of the side seam weld 132.

Scrim 108, but preferably not elastic is severed prior to side sealing. Once the web of material 120 passes through the sealing device 152, each individual garment 150 now has a separate scrim 108 located in the front waist 128 and the back waist 130. To accomplish this sealing process, the sealing device 152 preferably comprises a heat compression tool 156 and an anvil 158, which create a zone of penetrating heat that causes the elastic strands to melt and sever. The scrims are secured in place within the waists 128 and 130. The side seams 132 are formed but without any of the elastic material located in the regions 132. Thus, when the individual garments 150 are cut, concern of unnecessarily and improperly cutting the elastic scrims 108 is minimized. Even if the elastic strands of the scrim 108 are melted or severed past the seam weld 132 and into the front waist 128 or back waist 130, the scrim 108 will still maintain the desired elasticity and shape of the scrim 108.

Figure 6:
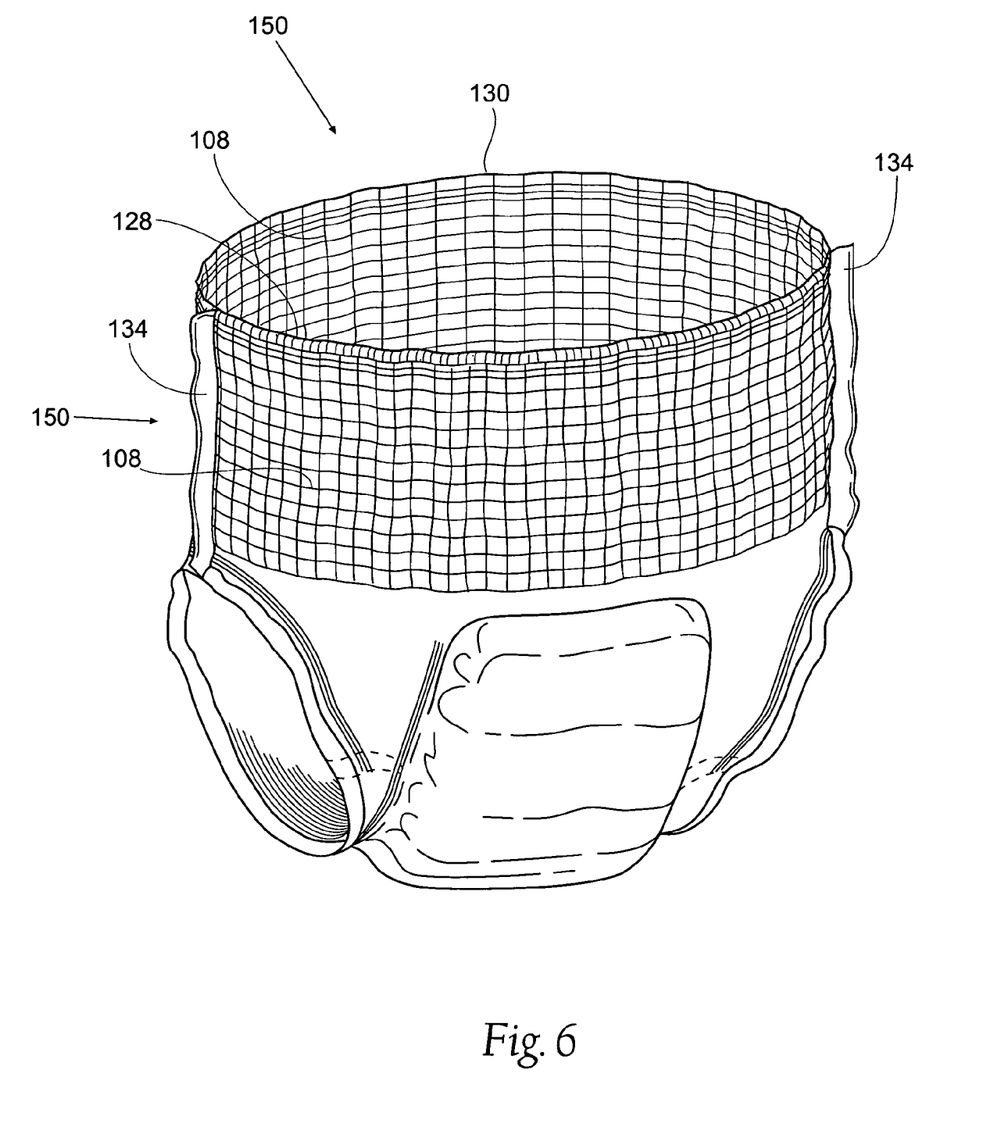
FIG. 6 is a perspective view of an embodiment of an undergarment formed according to the present invention.

FIG. 6 shows a perspective view of the finished undergarment 150. The scrim 108 is shown with an unbroken continuity through both the front waist 128 and the back waist 130. The heat-sealing process noted above has formed solid seals 134 that are free of elastic material while still maintaining elasticity in the front waist 128 and the back waist 130.

Figure 7:
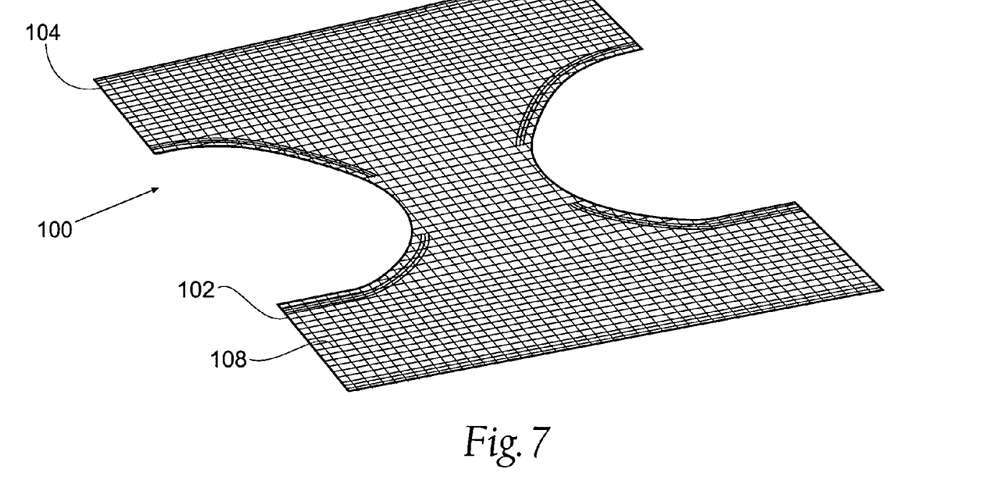
FIG. 7 shows a second embodiment of a layout formed according to the present invention.
Figure 8:
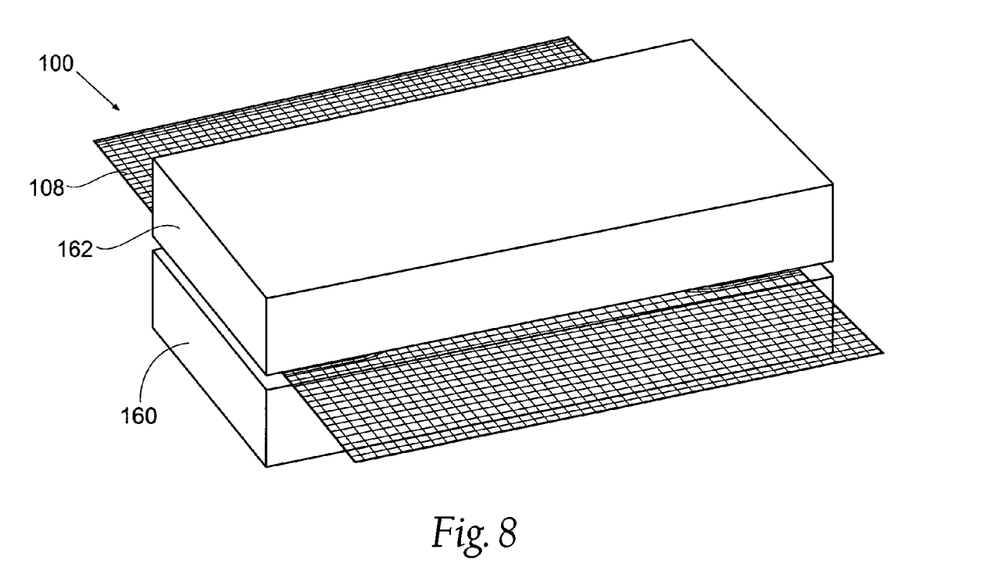
FIG. 8 shows a schematic of a step in the present invention to form non-elastic areas.

FIGS. 7 and 8 show another possible embodiment of the present method. Previously, as shown in FIG. 2, an individual scrim 108 is applied to both the first half 102 and the second half 104 of the blank 100. The perspective view of FIG. 6 shows an alternative embodiment to the arrangement of FIG. 2. Instead of separate scrims applied to each half, one large scrim 108 is placed over the entire blank 100. The scrim 108 would be layered similarly as described above in FIG. 3. However, because there is only one scrim to be aligned instead of two separate scrims, precision is not as important. Likewise, since the scrim may be provided for the process as one web of material, the additional step of cutting the scrip to be applied to each of the first and second half of the blank is no longer necessary.

FIG. 8 denotes a schematic representation of a further processing of the blank 100 as portrayed in FIG. 7. Once the scrim 108 is adhered within the blank 100, a second heat compression tool 160 and a second anvil 162 compress the blank 100 in a predetermined area where elastic material is not desired. As shown in FIG. 7, the second compression tool 160 and the second anvil 162 would melt and sever an area of the scrim 108 so that the blank 100 resembles the blank 100 of FIG. 1 and eventually the undergarment 150 of FIG. 5. While a second tool 160 and anvil 162 are contemplated, it is possible to combine all the required heating and severing steps with a single tool and anvil.

The description of a second tool anvil is used as an example to show the elastic material may be removed from any portion of the undergarment. For example, undergarments, especially children's diapers, are commonly designed with pictures or patterns on the front and/or rear of the diaper. Forming diapers without elastic material in these areas prevents the pictures or patterns from being distorted, as diaper has a tendency to bunch up if elastic is present in these areas. According to this invention, a second tool anvil could be used to remove the elastic material from the area of the undergarment where the picture or pattern would be located.

Likewise, depending on specific designs, more than two tool/anvil arrangements may be incorporated into the process. For instance, the leg elastics 126 (see FIG. 3) may be replaced with a scrim design, which may be cause for a different or modified tool/anvil combination.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention

I claim:

1. A method of cutting elastic strands between layers of carrier webs comprising;
   providing a first layer of carrier web material;
   providing a second layer of carrier web material;
   applying adhesive to at least one of said layers of carrier material across a first area;
   providing at least one elastic scrim area in a second area, the second area including the first area, and having a machine direction dimension and a cross-machine direction dimension, the scrim having a predetermined tension and applying the elastic scrim to the one of said layers of carrier web material with adhesive applied thereto;
   compressing the first and second layers together such that the scrim is secured between the layers; and
   severing the elastic scrim in portions of second area but not in the first area, by passing the web through a severing device comprising a heat compression tool and an anvil and compressing the web in the second area, thereby allowing the elastic scrim to deactivate in the second area but not the first area.

2. The method of claim 1 further comprising:
   removing the elastic scrim in an additional predetermined area of the web materials by passing the web through a second severing device made of a second heat compression tool and a second anvil and compressing the area where elastic material is not desired.

3. The method of claim 1 further comprising:
   folding the compressed web material in a longitudinal direction;
   sealing the side seams using a sealing device comprising at least one of a heat compression tool, an ultrasonic device, and an anvil;
   cutting the web material along the side seams to form discrete diapers using a cutting device.

4. The method of claim 3 further comprising:
   folding the compressed web material in a longitudinal direction;
   sealing the side seams using a sealing device comprising a heat compression tool and an anvil;
   cutting the web material along the side seams to form discrete diapers using a cutting device.

5. A method of cutting elastic strands between layers of carrier webs comprising:
   providing a first layer of carrier web material;
   providing a second layer of carrier web material;
   applying adhesive to at least one of said layers of carrier material to a first area where stretch is desired, and not applying adhesive to a second area, the second area defining where stretch is not desired;
   providing two sections of elastic scrim across both the first area and the second area, the elastic scrim having a predetermined tension;
   applying each of said sections of elastic scrim to a predetermined location on the one of said layers of carrier web material with adhesive applied thereto;
   compressing the first and second layers together such that the scrim is secured between the layers thereby creating a composite having two scrim areas;
   folding said composite to place said two scrim areas into proximity with one another; and
   severing the elastic scrim sections in the second area by passing the web through a severing device comprising a heat compression tool and an anvil and compressing the composite in the second area, thereby severing the elastic scrim sections in both the machine direction dimension and the cross-machine direction dimension across the second area, leaving the elastic scrim of the second area deactivated.

6. The method of claim 5 further comprising:
   removing the elastic scrim in an additional predetermined area of the web material by passing the web through a second severing device made of a second heat compression tool and a second anvil and compressing the area where elastic material is not desired.

7. The method of claim 5 further comprising:
   folding the compressed web material in a longitudinal direction;
   sealing the side seams using a sealing device comprising a heat compression tool and an anvil;
   cutting the web material along the side seams to form discrete diapers using a cutting device.

8. The method of claim 7 further comprising:
   folding the compressed web material in a longitudinal direction;
   sealing the side seams using a sealing device comprising a heat compression tool and an anvil;
   cutting the web material along the side seams to form discrete diapers using a cutting device.

9. A method of cutting elastic strands between layers of carrier webs comprising:
   providing a first layer of carrier web material;
   providing a second layer of carrier web material;
   applying intermittent adhesive to one of said layers of carrier material thereby defining an elasticized zone where adhesive has been applied and a non-elasticized zone where adhesive has not been applied;
   providing a large elastic scrim across the elasticized zone and the non-elasticized zone with a predetermined tension and applying the elastic scrim to the one of said layers of carrier web material with adhesive applied thereto;
   compressing the first and second layers together such that the scrim is secured between the layers; and
   severing the elastic scrim area across the non-elasticized zone by passing the web through a severing device comprising a heat compression tool and an anvil and compressing the web across the elasticized zone and the non-elasticized zone thereby leaving the elastic scrim of the non- elasticized zone not adherent to the first or second layers of carrier web material, where elastic material is not desired.

10. The method of claim 9 further comprising:
    removing the elastic scrim in an additional predetermined area of the web material by passing the web through a second severing device made of a second heat compression tool and a second anvil and compressing the area where elastic material is not desired.

11. The method of claim 9 further comprising:
    folding the compressed web material in a longitudinal direction;
    sealing the side seams using a sealing device comprising a heat compression tool and an anvil;
    cutting the web material along the side seams to form discrete diapers using a cutting device.

12. The method of claim 11 further comprising:
    folding the compressed web material in a longitudinal direction;
    sealing the side seams using a sealing device comprising a heat compression tool and an anvil;
    cutting the web material along the side seams to form discrete diapers using a cutting device.

* * * * *